United States Patent [19]
Ohnuma et al.

[11] Patent Number: 5,129,790
[45] Date of Patent: Jul. 14, 1992

[54] PLUNGER PUMP

[75] Inventors: Sadabumi Ohnuma, Hitachi; Genzo Hirata, Katsuta; Yoshiaki Yamada, Katsuta; Hiromi Takiuchi, Katsuta; Sachio Tomimatsu, Katsuta; Wataru Kato, Katsuta, all of Japan

[73] Assignee: Hitachi, Ltd., Tokyo, Japan

[21] Appl. No.: 672,318

[22] Filed: Mar. 20, 1991

Related U.S. Application Data

[63] Continuation of Ser. No. 409,138, Sep. 19, 1989, abandoned.

[30] Foreign Application Priority Data

Sep. 21, 1988 [JP] Japan .................. 63-235032

[51] Int. Cl.$^5$ .................. F04B 21/00; F01B 31/00
[52] U.S. Cl. .................. 417/63; 92/86.5
[58] Field of Search .................. 92/82, 83, 86, 86.5; 417/568, 63

[56] References Cited

U.S. PATENT DOCUMENTS

| 2,330,781 | 9/1943 | Langmyhr et al. .................. 92/86.5 |
| 3,914,752 | 10/1975 | Howard et al. .................. 340/242 |
| 3,943,717 | 3/1976 | Schexnayder .................. 92/86 |

FOREIGN PATENT DOCUMENTS

| 0095448 | 11/1983 | European Pat. Off. . |
| 2710778 | 9/1978 | Fed. Rep. of Germany . |
| 2805048 | 8/1979 | Fed. Rep. of Germany . |
| 3227052 | 1/1984 | Fed. Rep. of Germany . |

Primary Examiner—Richard A. Bertsch
Assistant Examiner—Howard R. Richman
Attorney, Agent, or Firm—Antonelli, Terry Stout & Kraus

[57] ABSTRACT

A plunger pump for supplying solution in accordance with an extrusion action of a plunger within a pump chamber. The plunger pump includes a cleaning chamber sealed by a seal member around and relative to the plunger, with a cleaning liquid inlet-side flow conduit and a cleaning liquid outlet-side flow conduit for communicating with the cleaning chamber, respectively. A mechanism isolates one of the inlet- and outlet-side flow conduits from the atmosphere and releases the other to an atmosphere under a condition where the cleaning liquid inlet- or outlet-side flow conduits are filled with the cleaning liquid. If the seal member in sliding contact with the plunger is degraded or aged, it is possible to observe a leakage of the liquid from the pump chamber along a sealing face between the seal member and the plunger.

8 Claims, 6 Drawing Sheets

PLUNGER PUMP

CROSS-REFERENCE TO RELATED APPLICATIONS

This application is a Continuation Application of U.S. application Ser. No. 409,138 filed Sep. 19, 1989, now abandoned.

BACKGROUND OF THE INVENTION

The present invention relates to a plunger pump, and more particularly to a plunger pump suitable for supplying solution or liquid by the extrusion action of the plunger within a pump chamber.

In a liquid chromatograph, solution is supplied at a high pressure by using a plunger pump. The supply of solution is carried out by the extrusion action of a plunger of the pump. In the use of the pump, a small amount of solution adheres to a peripheral wall of the plunger and leaks out of the pump chamber through a sliding contact seal portion of seal member with the plunger as the plunger is reciprocated. A problem of conventional systems resides in the fact that solid material precipitated from the leaking solution damages the seal member. In order to cope with this problem, in, for example, Japanese Patent Unexamined Publication 58-165581 corresponding to European Patent Publication No. 0095,448A1, an apparatus is proposed wherein, as shown in FIG. 8, an annular clearance 104 is formed around a plunger 101, with the annular clearance 104 being sealed between seal members 102 and 103. A cleaning liquid 106 is introduced into the clearance 104 through a channel 105, whereby the precipitated solid material is removed from the plunger 101.

Since the annular clearance 104 around the plunger 101 is narrow and a distance between the cleaning solution channel 105 and the seal member 105 is long, it is difficult to generate a sufficient cleaning liquid flow through the clearance 104 to clean the clearance 104. In addition, in the conventional apparatus, since the cleaning liquid 106 is supplied from a liquid reservoir 109 through a conduit 110, pump line 111 and conduit 112 to the channel 105, and is further discharged through a conduit 113 to a liquid reservoir 114, it is not possible to observe or detect leakage of liquid from the pump chamber 108, formed in the pump housing 107, due to a degradation of the seal member 102. Since it is not possible to observe or confirm the damage or degradation of the seal member 102, it is not possible to know a suitable time for replacement of the seal member 102.

SUMMARY OF THE INVENTION

An object of the invention is to provide a plunger pump which is capable of enabling an observation or confirmation of leakage of liquid from a pump chamber in the case where a seal member in sliding contact with the plunger is damaged or aged.

The above object can be attained by a plunger pump for supplying solution in accordance with an extrusion action of a plunger within a pump chamber, which plunger pump comprises a cleaning chamber sealed by a seal member around and relative to the plunger, with a cleaning liquid inlet-side flow conduit and a cleaning liquid outlet-side flow conduit for communicating with the cleaning chamber, respectively, and a mechanism for isolating one of the inlet-and outlet-side flow conduit from an atmosphere and releasing the other to the atmosphere under a condition where the cleaning liquid inlet-and outlet-side flow conduits are filled with the cleaning liquid.

In a plunger pump in accordance with the invention, it is possible to isolate from or release to the atmosphere one of the cleaning liquid inlet-side flow conduit and the cleaning liquid outlet-side flow conduit which are in communication with the cleaning chamber. The open ends of the two flow conduits are provided at least close to each other so that the flow path from the sample liquid injection inlet through the cleaning liquid inlet-side flow conduit and cleaning chamber to the cleaning liquid outlet-side flow conduit is kept filled with the cleaning liquid. In this case, since one of the conduits is isolated from the atmosphere even if the supply of the cleaning liquid is stopped, the cleaning liquid in the flow conduits is not discharged but is maintained under the static condition. Under this condition, if the seal member of the plunger is damaged or degraded, since the pressure within the pump chamber is higher than that within the cleaning chamber, the solution is leaked through the seal member from the pump chamber. An amount of solution corresponding to the volume of the solution leaked therefrom is discharged from the atmospheric released end of the cleaning liquid discharge conduit. It is possible to observe or confirm the damage or degradation of the seal member by the discharge of the liquid.

According to the present invention, in the plunger pump, since the same amount of liquid as that from the pump chamber is discharged from the atmospheric release end of the discharge conduit if the seal member of the plunger is degraded, it is possible to indirectly confirm the degradation of the seal member by observing the discharge of the liquid. It is thus possible to know the suitable replacement stage of the seal members.

In the case where it is desired to select the cleaning liquid inlet-side flow conduit and cleaning liquid outlet-side flow conduit within a predetermined relative range in height, both the inlet-and outlet-side conduits may be opened to the atmosphere.

Namely, according to the invention, a plunger pump for supplying solution in accordance with an extrusion action of a plunger within a pump chamber is provided, with the cleaning chamber sealed by a seal member around and relative to the plunger, a cleaning liquid inlet-side flow conduit and a cleaning liquid outlet-side flow conduit for communicating with the cleaning chamber, respectively, and a cleaning liquid injection block having a releasing chamber for releasing, to an atmosphere, one of the cleaning liquid inlet-side flow conduit and the cleaning liquid outlet-side flow conduit. One end of the cleaning liquid inlet-side flow conduit and one end of the cleaning liquid outlet-side flow conduit are opened to the releasing chamber of the cleaning liquid injection block, and the one ends thereof are close to each other in level.

Another object of the present invention resides in providing a plunger pump for allowing a sufficient flow of the cleaning liquid over an entire region of the clearance around the plunger up to the seal member.

The above and other objects are attained by providing a plunger pump for supplying solution in accordance with an extrusion action of a plunger within a pump chamber, comprising a cleaning chamber sealed by a seal member around and relative to the plunger, and a cleaning liquid inlet-side flow conduit and a cleaning liquid outlet-side flow conduit for communicating with the cleaning chamber, respectively, wherein a distance between a circumferential wall of the cleaning chamber and a circumferential wall of the plunger is longer than a distance between a wall of the pump chamber in a plunger movement path and a circumferential wall of the plunger.

BRIEF DESCRIPTION OF THE DRAWINGS

The foregoing and other objects, features and advantages of the present invention will become more apparent by the following description in connection with the accompanying drawings wherein.

DESCRIPTION OF THE PREFERRED EMBODIMENTS

Figures 1A, 1B:
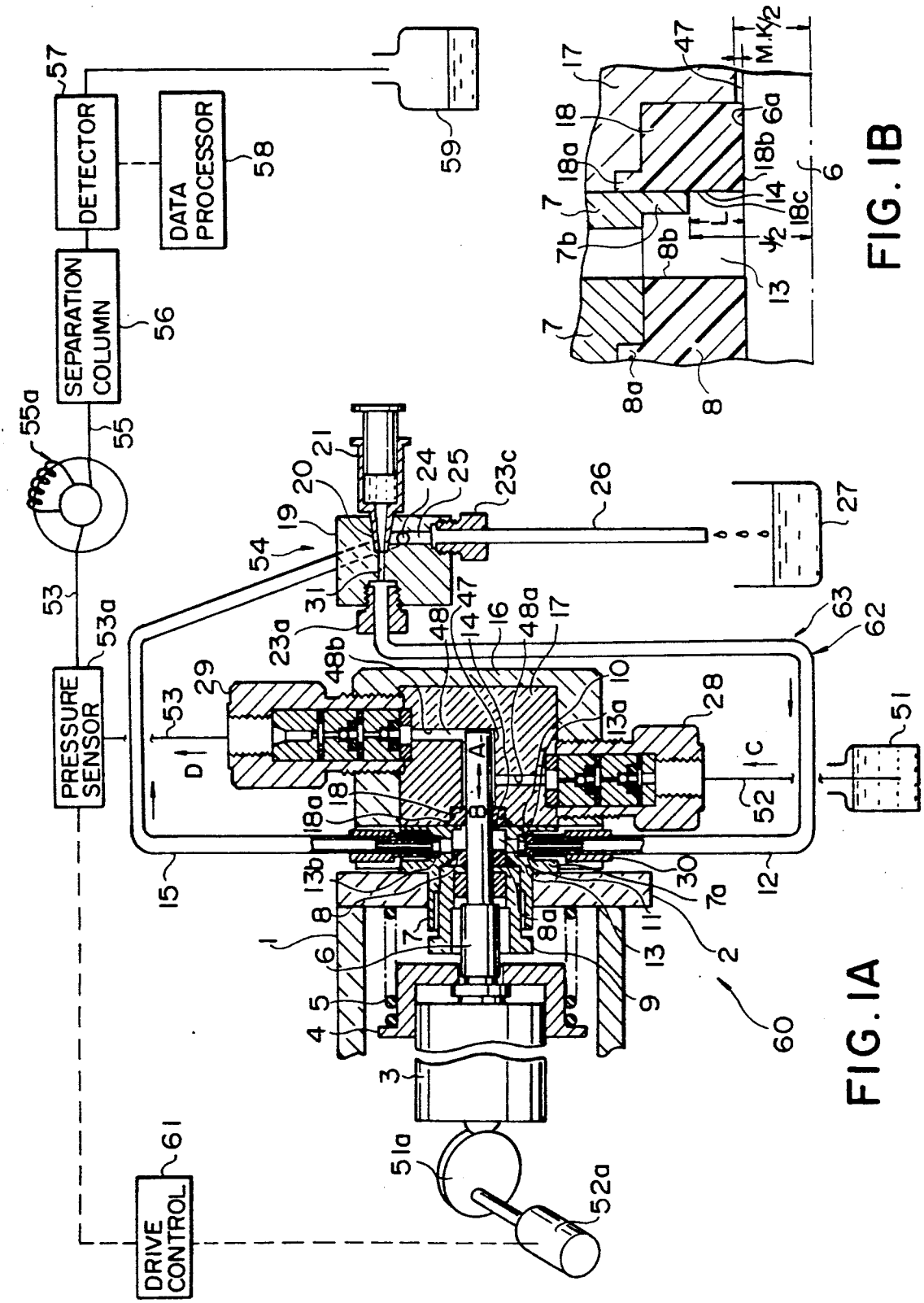
FIG. 1A is a partial schematic cross sectional view of a liquid chromatograph including a pump in accordance with an embodiment of the invention.
FIG. 1B is an enlarged cross-sectional view showing a cleaning chamber shown in FIG. 1A.
Figure 2:
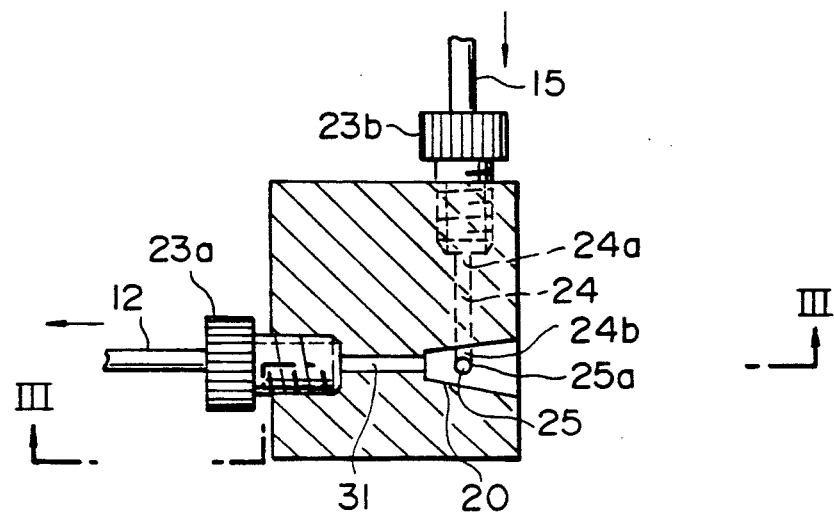
FIG. 2 is a cross-sectional plan view of a cleaning liquid injection block of FIG. 1A taken along the line II—II in FIG. 3.
Figure 3:
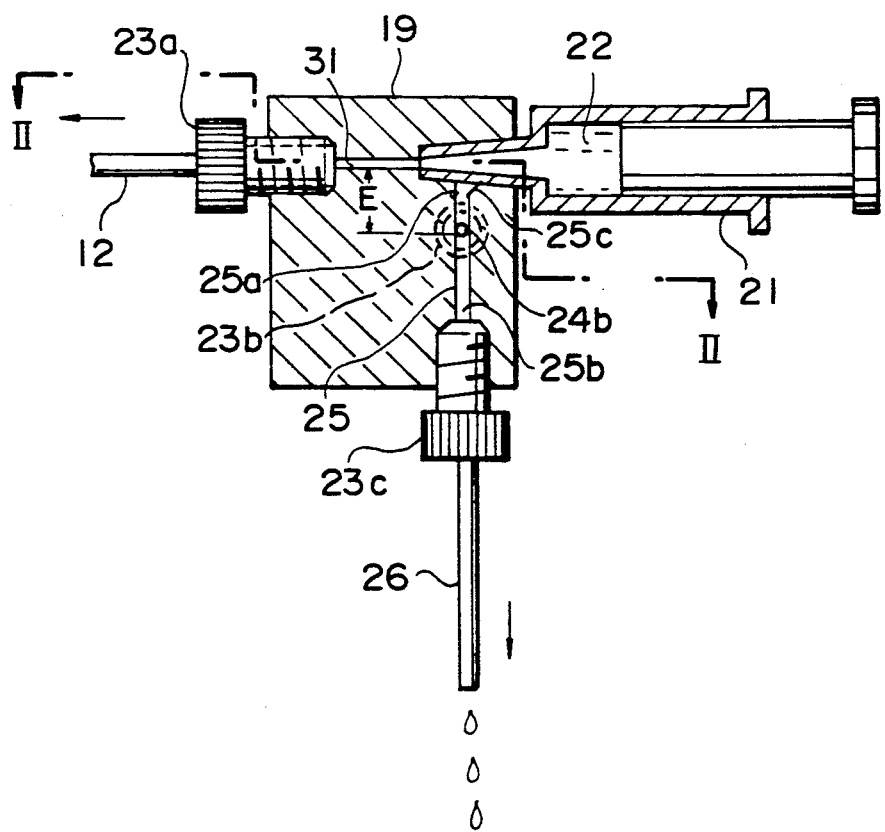
FIG. 3 is a cross-sectional view taken along the line III—III in FIG. 2, showing the condition with a cleaning liquid injector mounted on the cleaning injection block.

Referring now to the drawings wherein like reference numerals are used throughout the various views and, more particularly, to FIG. 1A, 1B, 2 and 3, according to these figures, a liquid chromatograph using a plunger in accordance with the present invention includes a stay plate 2 fixed to a pump case 1, with a bearing guide 7 being securely inserted into a hole of the stay plate 2 in a coaxial relationship with respect to the pump case 1 and the hole 2 of the stay plate 2, and with a bearing 9 being fixed to the bearing guide 7 in a coaxial relationship thereto. A slider 3 and a plunger 6 are provided along a center axis of the bearing 9 so that a rotational motion of an output shaft of a motor 52a is converted into a reciprocating motion of the slider 3 by a pump cam 51a. The plunger 6 is fixed to an end face of the slider 3 through a spring 5 and a spring seat or retainer 4, so that the slider 3 and the plunger 6 are simultaneously reciprocated in directions of the arrows A, B together with the spring seat 4 under the elastic force of the spring 5. A seal member 8, of synthetic resin, is inserted into the bearing guide 7. A flange portion 8a of the seal member 8 is interposed between the guide 7 and the bearing 9 made of stainless steel and synthetic resin. The seal member 8 is secured to the bearing 9 by suitable fasteners such as, for example, screws, (not shown). A packing 10 and a cleaning liquid inlet-side flow conduit 12 engaged with a joint 11 are inserted into a hole 13a of the bearing guide 7 which is in communication with a cleaning chamber 13. The packing 10 and the conduit 12 are fixed by a retainer screw 30. A cleaning liquid out-side conduit 15 is fixed to another hole 13b of the bearing guide 7 in the same manner. A cleaning chamber 13 is formed in communication with the cleaning liquid inlet-side flow conduit 12 and the cleaning liquid outlet-side flow conduit 15. A seal member 18 fitted around the plunger 6 is inserted in an enlarged diameter hole formed in the central portion of a pump head 17 that is made of ceramic and inserted into a pump head holder 16. The seal member 18 is used to isolate the cleaning chamber 13 filled with the cleaning liquid from a pump chamber 48 through which the carrier solution flows. A suction valve 28 and a discharge valve 29 are disposed, respectively, in a carrier liquid introduction path 48a communicating a carrier liquid reservoir portion 51 through a conduit 52 with the pump chamber 48 and a carrier liquid discharging path 48b communicating the pump chamber 48 with the carrier liquid discharge conduit 53. The pump head 17 and the holder 16 are fitted to a flanged portion 7a of the bearing guide 7, with inlet and outlet valves 28, 29 being mounted thereon and being detachably fixed by fastening means such as bolts to the stay plate. A flanged portion 18a of the seal member 18 is clamped between the head 17 and the bearing guide 7.

A cleaning liquid supply mechanism generally designated by the reference numeral 54 serves to supply the cleaning liquid 22 and to connect other communication conduits. The cleaning liquid supply mechanism 54 has a cleaning liquid supplying block 19 having a communication hole 31 communicating a cleaning liquid supply inlet 20 with the inlet-side flow conduit 12 mounted by a retainer screw head 23a, an outlet-side discharge hole 24 communicated at one end 24a with the outlet-side flow conduit 15 mounted by a retainer head 23b, and an atmospheric vent chamber or hole 25 opened at its upper end 25a to the supply inlet 20, communicating at its middle portion to an end 24b of the discharge hole 24, and communicating at its lower end 25b with a discharge conduit 26 mounted through a retainer screw head 23c. An injector 55a injects a chromatographic sample to be analyzed into the carrier liquid flowing through the conduit 53. A separation column 56 is provided along with a detector 57 detecting sample components separated in the column 56 and a data process 58 processes data detected by the detector 57. A reservoir 59 is provided for the measured liquid, i.e., drain, with a carrier liquid pressure sensor 53a being interposed in the conduit 53, and a motor 52a being controlled by a motor drive controller 61 so that the pressure detected by the sensor 53a is kept in a predetermined level of, for example, 100 to 400 kgf/cm$^2$.

In operation of the plunger pump generally designated by the reference numeral 60, when the rotation emulsion of the motor 52a is converted into reciprocating motion of the slider 3 by the pump cam 51a, the plunger 6 is also reciprocated in the direction of the arrows A and B along a plunger reciprocation path 47 in synchronism therewith. Since the pump chamber 48 is sealed by the seal member 18, as the plunger 6 is linearly moved in a direction of the arrow B, the discharge valve 29 is closed so that the carrier solution is suctioned from the suction valve 28 through the conduit 52 to the pump chamber 48 in a direction of the arrow C. On the other hand, when the plunger 6 is linearly moved in the direction of the arrow A, the suction valve 28 is closed so that the carrier solution is discharged from the pump chamber 48 in a direction of an arrow D through the discharge valve 29. The rotational drive of the motor 52a during the suction and discharge is controlled by the pressure sensor 53a and the drive control 61 to thereby control the feed or discharge of the carrier liquid flowing through the conduit 53.

In a field of liquid chromatography, for example, a biochemical field, since an aqueous solution of compounds of alkaline metal or alkaline earth metal is used as the solution, if the seal member is damaged or aged, the solution leaks through the sliding surfaces between the plunger 6 and the sealing member 18 to the outside of the pump chamber 48, so that the solid salts, i.e. the above-mentioned compounds are precipitated at the leakage area. As a result, the precipitated solid material accelerates a wear of the seal member 18 made of synthetic resin, so that the seal member 18 is damaged, whereby a service life thereof is shortened. For the purpose of overcoming the above-noted defect, the cleaning chamber 13 and the cleaning liquid inlet- and outlet-side flow conduits 12 and 15 in communication with the cleaning chamber 13 are provided. The cleaning chamber 13 is sealed by the seal member 8 provided on a side of the seal member 18 opposite to the pump chamber 48. In the plunger pump 60, an inner diameter J (radius J/2) of the flanged portion 7b of the bearing guide 7 is larger than an inner diameter K (radius K/2) of the plunger path 47 in the pump head 17. Namely, a distance L between an inner circumferential wall of the bearing guide 7, that is, the circumferential wall of the cleaning chamber 13, and a circumferential wall of the plunger 6 is longer than a distance M between the pump chamber wall in the plunger path 47 and the circumferential wall of the plunger 6. In other words, since the seal member 18 is supported only in the outer circumferential region of the end face 18c by the radially inwardly extending flanged portion 7b of the bearing guide 7, an inner circumferential region 14 of the end face 18c of the seal member 18 may be easily brought into direct contact with the cleaning liquid 22 within the cleaning chamber 13. In the same manner, the seal member 8 may be brought into direct contact with the cleaning liquid 22 within the cleaning chamber 13 in the overall region of the end face 8b of the seal member 8. The cleaning chamber 13 is used to dilute the solution leakage from the interface 18b of the seal member 18 and to dissolve the precipitated salts if any.

When the cleaning liquid injector 21, which sealingly contains the cleaning liquid 22, is inserted into the cleaning liquid supply inlet 20 of the cleaning liquid injection block 19, the atmospheric vent chamber 25, intersecting the taper portion of the cleaning liquid injection outlet 20, is closed at the opening 25a. When the cleaning liquid 22 is injected by the action of the injector 21, the cleaning liquid 22 is supplied from the communication hole 31 past the cleaning liquid inlet-side conduit so that, in the cleaning chamber 13, the cleaning liquid 22 is in direct contact with the interface 14 of the seal member 18 to dilute or dissolve the precipitated solid salts if any. After the cleaning liquid 22 has flowed through the cleaning chamber 13, the cleaning liquid flows through the cleaning liquid outlet-side conduit 15, located opposite the inlet, and through the cleaning liquid outlet-side discharge hole 24 to the atmospheric vent chamber 25. The cleaning liquid 22 is further discharged from an atmospheric release end of the cleaning liquid discharge conduit 26 to be collected in a drain bottle 27. When the supply through the injector 21 is stopped under the condition that the cleaning liquid 22 fills a path 62 from the cleaning liquid injection inlet 20 to the end of the cleaning liquid discharge conduit 26, the injected liquid 22 from the injection inlet 20 to the lower end of the discharge conduit 26 is maintained in a static condition, since the injection inlet 20 is closed by the injector 21. Under such a condition, when the seal member 18 is damaged, a pressure in the flow path for feeding the carrier liquid, i.e., the pump chamber 48 is higher than a pressure of the cleaning chamber 13, so that the carrier solution leaks from the pump chamber 48 to the cleaning chamber 13 through the sliding contact surfaces 18b, 6a of the seal member 18 and the plunger 6. Since the injection hole 20 is closed by the injector 21, the leakage carrier liquid will press the cleaning liquid 22 in the flow path 62 toward the opening 24b, so that the amount of cleaning liquid corresponding to the leaked amount is discharged from the atmospheric release end of the cleaning liquid discharge conduit 26. Thus, it is possible to observe or confirm the damage or degradation of the seal member 18.

When the cleaning liquid injector 21 is removed from the cleaning liquid injection inlet 20 under the condition where the flow path 62 is filled with the cleaning liquid 22, the liquid 22 having filled the relatively large diameter atmospheric vent chamber 24 (for example, inner diameter of 2 mm), the cleaning liquid discharge conduit 26 is discharged to the drain bottle 27 to be released to the atmosphere. Since the inlet side communication 31 and the outlet side discharge hole 24 are relatively thin (for example, inner diameter of 1 mm) and a height difference E (FIG. 3) between the open end 24b of the discharge hole 24 and the inlet side communication hole 31 is small (for example, 5 mm) in comparison with a high pressure maintained by the surface tension of the cleaning liquid 22, the cleaning liquid 22 filling a path 63 from the cleaning liquid inlet side conduit 12 through the cleaning liquid outlet side conduit 15 to the discharge hole 24 remains in the static condition with the flow path 63, even if the injector 21 is removed and the injection inlet 20 is released to the atmosphere. In the case where the seal member is damaged so as to cause a liquid leakage from the seal surface 18b, because of the height difference E between the inlet side hole 31 and the end 24b of the discharge hole 24, the cleaning liquid is discharged from the cleaning liquid discharge hole 24 so that the cleaning liquid 22 is discharged from the discharge conduit 26. It is thus possible to observe or confirm the damage or degradation of the seal member 18.

Namely, under the condition where the cleaning liquid injector 2; is inserted into the cleaning liquid injection block 19 or is removed therefrom, if the sealing member 18 is damaged or degraded, it is possible to visually observe the leakage as a drop of the cleaning liquid 22 from the discharge conduit 26.

In addition, if the flow path 62 or 63 is filled with cleaning liquid 22, since the interface 14 of the seal member 18 is directly confronted with the cleaning chamber 13 over a wide region, even if the carrier liquid 22 adhering to the outer circumferential surface 6a of the plunger 6 gradually and slightly leaks from the pump chamber 48 in accordance with the movement of the plunger 6 in the direction of the arrow B when the seal member is not damaged, the salts end or the like contained in the leaked carrier liquid are dissolved and diluted by the cleaning liquid 22 in the cleaning chamber 13. Thus, it is possible to suppress the precipitation of the solid material to thereby lengthen the service life of the seal member 18. Where the carrier liquid leaks along the seal surface 18b and a flow resistance F1 from the cleaning chamber 13 to the end 24b of the discharge hole 24 is much higher than a flow resistance F2 from the cleaning chamber 13 to the open end of the inlet side hole 31, the cleaning liquid 32 would be discharged from the inlet side hole 31. Therefore, it is preferable to provide the taper portion 25c at the upper end 25a of the atmospheric vent chamber 25 in order to have the cleaning liquid 22 drop from the discharge conduit 26 in this case as well.

Figure 4:
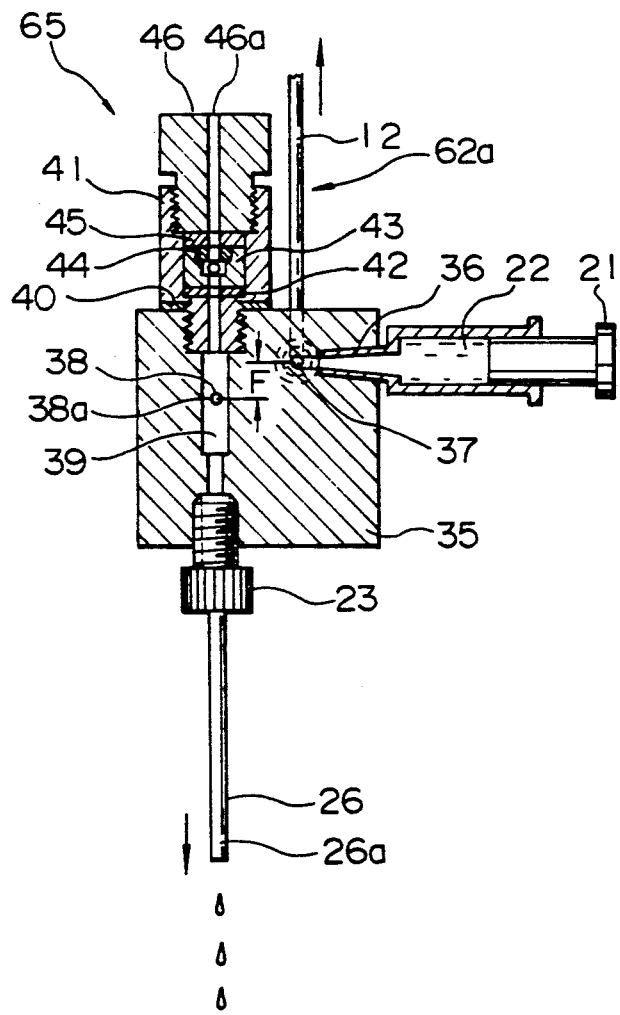
FIG. 4 is a cross-sectional view of another embodiment of a cleaning liquid injector block with the cleaning liquid injector mounted thereon.
Figure 5:
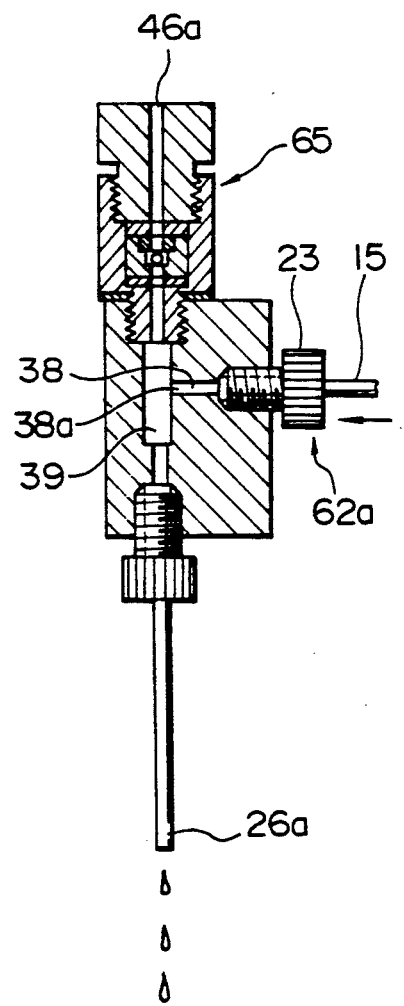
FIG. 5 is a cross-sectional view of FIG. 4.

In FIGS. 4 and 5, the cleaning liquid injection inlet 36 is formed in a cleaning liquid injection block 35 in communication with the cleaning liquid inlet-side flow conduit 12, with the cleaning chamber and the cleaning liquid outlet-side flow conduit 15 communicating through a communication hole 37. Further, order to readily release cleaning liquid outlet-side discharge hole 38 to the atmospheric pressure, the discharge port 38 intersects with an atmospheric vent chamber 39 having a larger diameter than that of the cleaning liquid outlet-side discharge hole 38. A check valve assembly generally designated by the reference numeral 65 is mounted at an upper part of the atmospheric vent chamber 39 on a cleaning liquid injection block 35 through a packing 40. The check valve assembly 65 is constructed by retaining a packing with a retainer screw 46 after inserting a valve packing 42 and a valve body 43 into a holder 41 and pressingly inserting a check valve member 44 in the center of the valve body 43. The cleaning liquid discharge conduit 26 is mounted at a lower end of the atmospheric vent chamber 39 to thereby communicate an upper end 46a of the check valve assembly 65, the atmospheric vent chamber 39, and a lower end 26a of the cleaning liquid discharge conduit 26 to the atmosphere.

Under such condition as described above, when the cleaning liquid ejector 21, filled with the cleaning liquid 22, is inserted into the cleaning liquid injection inlet 36 and when the cleaning liquid 22 is injected, the cleaning liquid fills the cleaning liquid inlet-side conduit 12, the cleaning chamber 13, the cleaning liquid outlet-side conduit 15 to the tip end 26a of the cleaning liquid discharge conduit 26. However, when the supply of the cleaning liquid 22 is stopped, the check valve member 44 is opened to the atmospheric pressure, so that the cleaning liquid 22 in the atmospheric vent chamber 39 and the cleaning liquid discharge conduit 26 is discharged down to the atmosphere or drain bottle 27, while cleaning liquid 22 in the flow path 62a from the injection inlet 36 to the open end 38a of the discharge hole 38 remains in the static condition.

Under the static condition, if the seal member 18 is damaged or aged, the carrier solution leaks from the pump chamber 48 along the seal surface 18b to the cleaning chamber 13. At this time, the cleaning liquid 22 within the flow path 62a is pressed and the check valve member 44 is closed, so that the cleaning liquid 22, filled in the cleaning liquid output-side discharge hole 38, is discharged from the atmospheric release end 26a of the cleaning liquid discharge conduit 26. It is thus possible to observe or confirm the damage or degradation of the seal member 18.

Since the inlet-side hole 37 and the discharge hole 38 are thin (for example, an inner diameter of about 1 mm), the atmospheric vent chamber 39 and the discharge conduit 26 are large in diameter (for example, inner diameter of about 2 mm), and the height difference F between the holes 37 and 38 is relatively small (for example, about 5 mm), the cleaning liquid 22 is maintained under the static condition, even if the cleaning liquid injector 21 is removed from the cleaning liquid injection block 35. Under this condition, if the seal member 18 is damaged and the carrier liquid leaks along the seal surface 18b, the cleaning liquid 22 is discharged through the discharge hole 38 and the discharge conduit 26 corresponding to the leakage amount of the carrier liquid along the sliding contact surface 18b of the seal member 18. It is thus possible to observe or confirm the damage or degradation of the seal member 18. Namely, in any of the cases where the cleaning liquid injection 21 is inserted into or removed from the cleaning liquid injection inlet 36, it is possible to visually observe the liquid leakage, whenever the seal member 18 is damaged or degraded.

Figure 6:
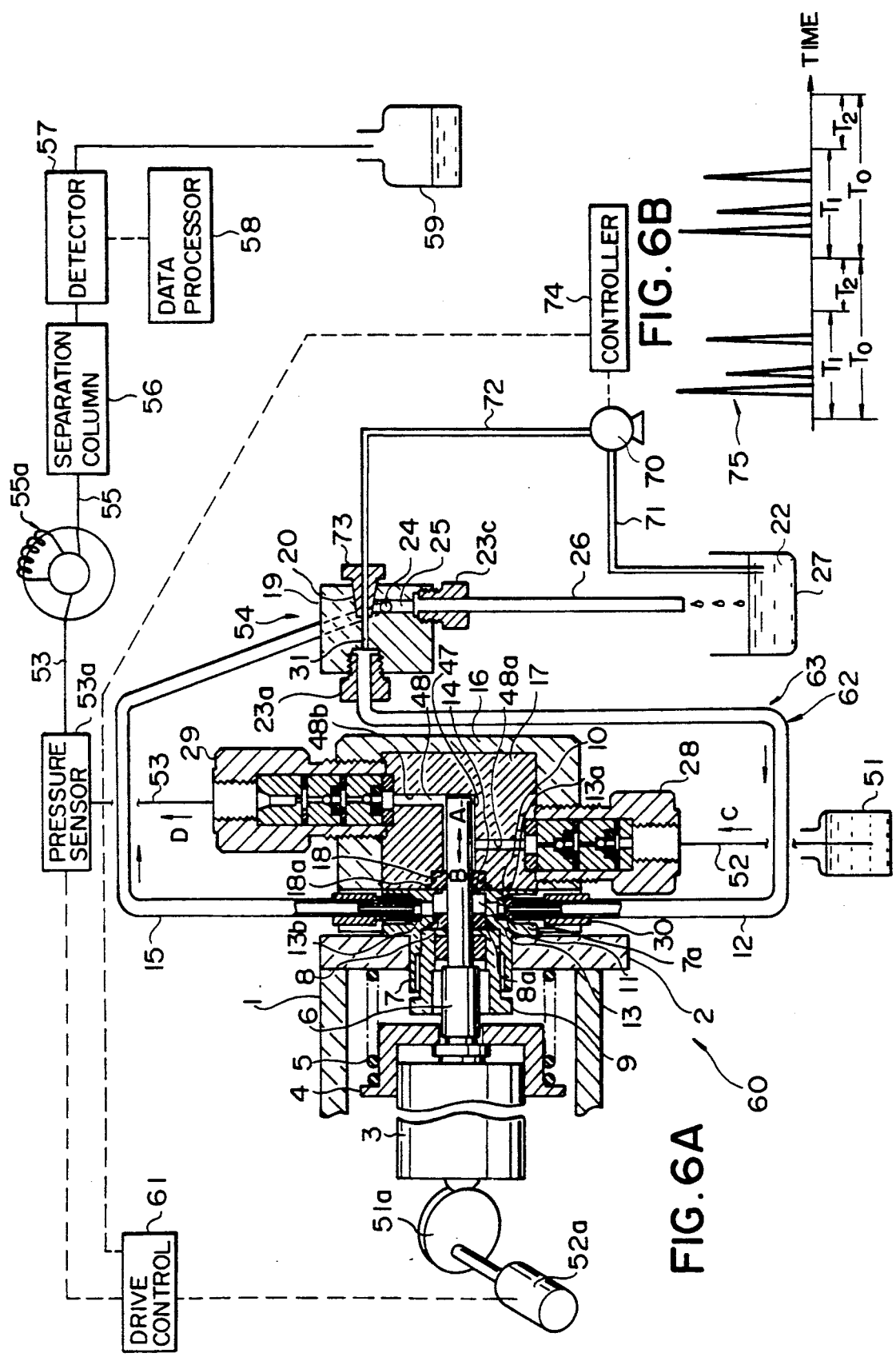
FIG. 6A is a partially schematic cross-sectional view of a modification of the chromatograph of FIG. 1A.
FIG. 6B is a time chart illustrating the operation control of the apparatus shown in FIG. 6A.

Incidentally, it is possible to perform the intermittent injection of the cleaning liquid 22 with a pump 70 as shown in FIG. 6A instead of using the injector 21. In this case, the pump 70 is used to suction the cleaning liquid 22 from the reservoir 27 through a conduit 71, and to feed the cleaning liquid to the communication hole 31 of the block 19 through a conduit 72 and a connector 73.

The drive control of the pump 70 is performed by a controller 74. For example, the pump 70 is continuously driven during the analyzing period T1 in one cycle T0 having a chromatogram 75, thereby continuously recirculating the cleaning liquid 22, and the pump 70 is stopped during a remaining period T2. Thus, it is possible to observe or confirm the leakage of the carrier liquid along the seal surface 18b of the seal member 18 by the drop of the cleaning liquid 22 from the conduit 26 during the period T2 when the pump 70 is stopped. In this case, the pump 70 and the motor 52a are driven in synchronism with each other.

Figure 7:
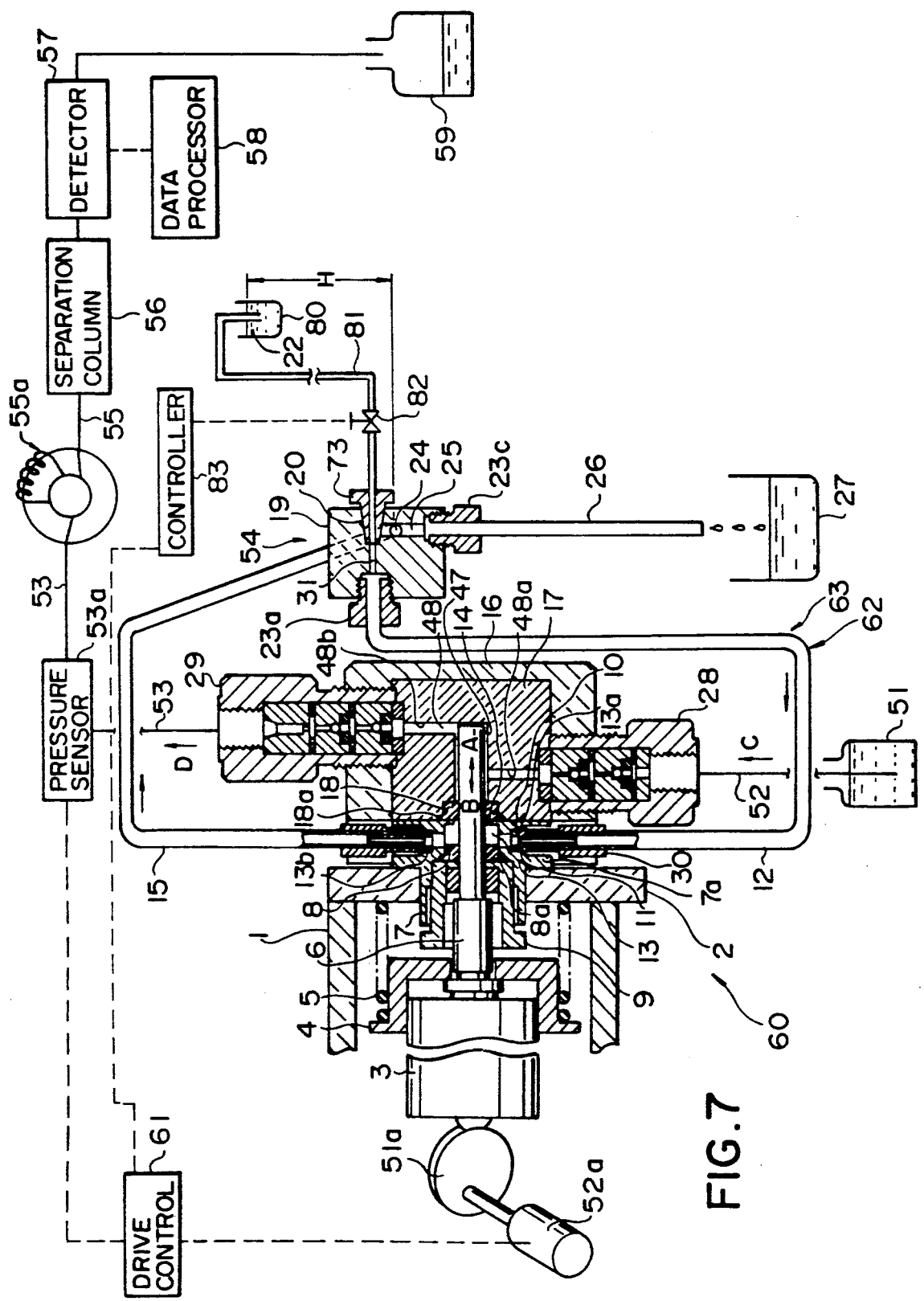
FIG. 7 is a partially schematic cross-sectional view of another modification of the chromatograph shown in FIG. 1A.
Figure 8:
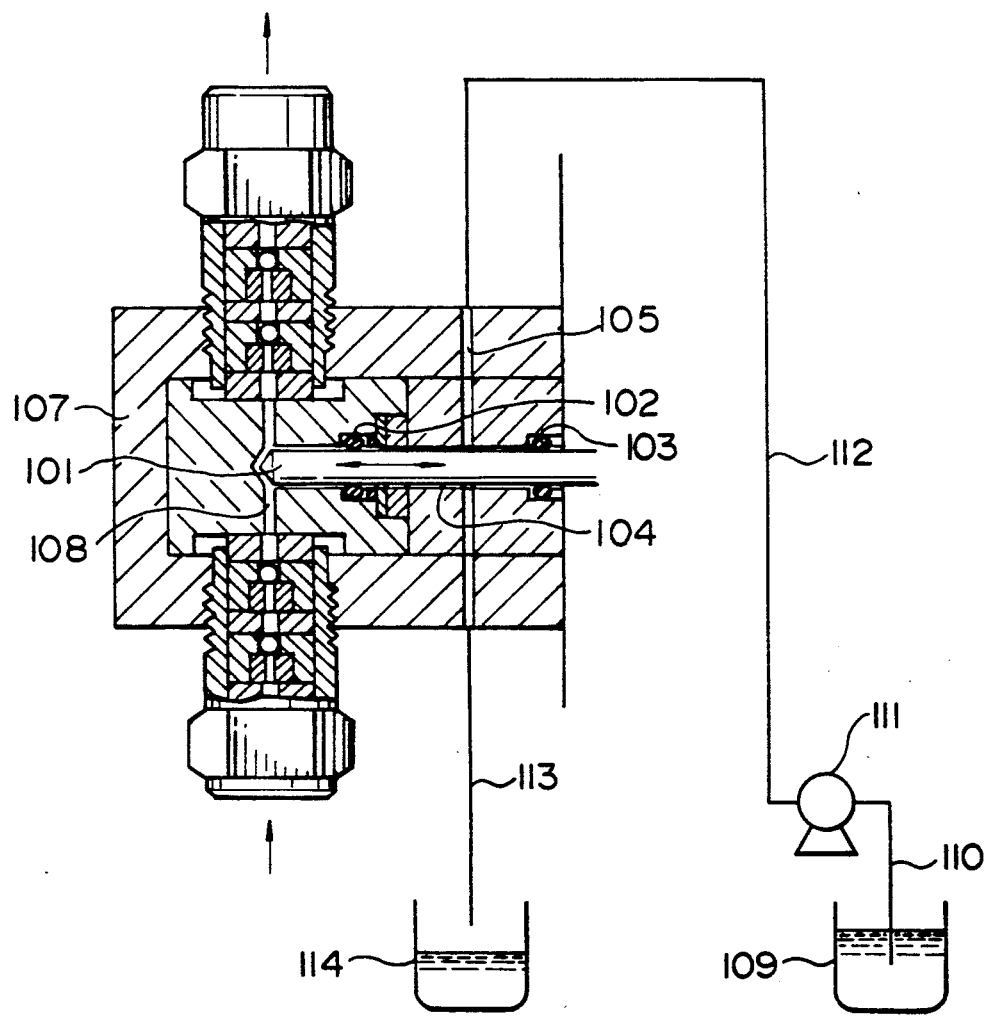
FIG. 8 is a cross-sectional view of a conventional plunger pump.

Furthermore, instead of using the cleaning liquid feeding pump 70, it is possible to provide a cleaning liquid reservoir 80 at a high level (for example, by a height H from the discharge hole 24), to provide an electromagnetic valve 82 in a conduit 81 between the liquid reservoir 80 and the connector 73 and to open the valve 82 during each analyzing period T1 explained in conjunction with FIG. 6B and close the valve 82 during each period T2 when the pump is stopped under the control of a controller 83, as shown in FIG. 7.

In this case, it is also possible to observe or confirm the leakage along the seal surface 18b of the seal member 18 by the drop of the cleaning liquid 22 from the conduit 26 during the period T2.

What is claimed is:

1. A plunger pump for supplying a carrier solution of a sample to be investigated by liquid chromatography in accordance with an extrusion action of a plunger within a pump chamber, the plunger pump comprising:

a cleaning chamber sealed from the pump chamber by a seal member around and relative to the plunger;

a cleaning liquid inlet-side flow conduit and a cleaning liquid outlet-side flow conduit respectively communicating with said cleaning chamber for directing a flow of cleaning liquid to said cleaning member for dissolving a solute of the carrier solution; and means for isolating said inlet-side flow conduit from an atmosphere and releasing said outlet-side flow conduit to the atmosphere when said cleaning liquid inlet-side and outlet-side flow conduits are filled with the cleaning liquid, and wherein a discharging end of said cleaning liquid outlet-side flow conduit is open to the atmosphere, so that a leakage of the carrier solution from the pump chamber into the cleaning chamber through the seal member due to degradation of the seal member is detected by a drop of the cleaning liquid from said discharging end of the outlet-side conduit to the atmosphere.

2. The plunger pump according to claim 1, wherein said isolating means includes a cleaning liquid introduction means for introducing the cleaning liquid to said inlet-side flow conduit.

3. The plunger pump according to claim 2, wherein said cleaning liquid introduction means comprises a cleaning liquid injector.

4. The plunger pump according to claim 2, wherein said cleaning liquid introduction means comprises a cleaning liquid supply pump.

5. A plunger pump according to claim 1, wherein a distance, at one side of the seal member, between a circumferential wall of said cleaning chamber and a circumferential wall of said plunger is longer than a distance, at the other side of the seal member, between a wall of said pump chamber in a plunger movement path and a circumferential wall of said plunger so that carrier solution accidentally leaking from the pump chamber into the cleaning chamber through the seal member is quickly diluted by the cleaning liquid therein.

6. A plunger pump according to claim 4, wherein said cleaning liquid supply pump is operational in response to signals received from a controller means.

7. A plunger pump according to claim 6, wherein said cleaning liquid supply pump serves to prevent flow of the cleaning liquid into said cleaning liquid inlet side flow conduit when said cleaning liquid supply pump is stopped.

8. A plunger pump according to claim 4, wherein said cleaning liquid supply pump serves to prevent flow of the cleaning liquid into said cleaning liquid inlet-side flow conduit when said cleaning liquid supply pump is stopped.

* * * * *